(12) United States Patent
Nishimiya et al.

(10) Patent No.: US 7,041,788 B2
(45) Date of Patent: May 9, 2006

(54) MULTIMERIZED HIGHLY FUNCTIONAL ANTIFREEZE PROTEIN

(75) Inventors: Yoshiyuki Nishimiya, Sapporo (JP); Sakae Tsuda, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 455 days.

(21) Appl. No.: 10/321,396

(22) Filed: Dec. 18, 2002

(65) Prior Publication Data

US 2004/0034195 A1    Feb. 19, 2004

(30) Foreign Application Priority Data

Dec. 28, 2001    (JP)    ............................. 2001/400607

(51) Int. Cl.
*A61K 38/00*    (2006.01)
*C07K 14/00*    (2006.01)

(52) U.S. Cl. ....................... 530/324; 530/333; 530/300

(58) Field of Classification Search ................ 530/350, 530/300
See application file for complete search history.

(56) References Cited

OTHER PUBLICATIONS

Christiansen et al. "The role of the MoFe protein alpha-125-Phe and beta-235-Phe residues in Azotobacter vinelandii MoFe protein Fe protein interaction". Journal of Inorganic Biochemistry. 2000. vol. 80, pp. 195-204.*

Sorlie et al. "Mechanistic features and structure of the nitrogenase alpha-Gln-195 MoFe protein". Biochemistry. 2001. vol. 40, pp. 1540-1549.*

USPOT sequence alignments for Wang et al. protein versus SEQ ID Nos: 2 and 4.*

Miura Kazunori et al: "NMR analysis of type III antifreeze protein intramolecular dimer: Structural basis for enhanced acativity", Journal of Biological Chemistry, vol. 276, No. 2, Jan. 12, 2001, pp. 1304-1310, XP002236044.

Wang Xin et al.: "Antifreeze peptide heterogeneity in an antarctic eel pout includes an unusually large major variant comprised of two 7 kDa type III AFPs linked in tandem.", Biochimica Et Biophysica Acta, vol. 1247, 'No. 2, 1995, pp. 163-172, XP002236045.

Wang Xin et al.: "Genomic basis for antifreeze peptide heterogeneity and abundance in an Antarctic eel pout: Gene structures and organization," Molecular Marine Biology and Biotechnology, vol. 4, No. 2, 1995, pp. 135-147, XP009007178.

Miura Kazunori et al.: "Determination of the solution structure of the N-domain plus linker of antarctic eel pout antifreeze protein RD3," Journal of Biochemistry (Tokyo), vol. 126, No. 2, Aug. 1999, pp. 387-394, XP002236046.

Graether Steffen P et al: "Quantitative and analysis of type III antifreeze protein structure and function," Journal of Biological Chemistry, vol. 274, No. 17, Apr. 23, 1999, pp. 11842-11847, XP002236047.

Ewart K V et al: "Structure, function and evolution of antifreeze proteins," CMLS Cellular and Molecular Life Sciences, vol. 55, No. 2, Feb. 1999, pp. 271-283, XP002236048.

* cited by examiner

*Primary Examiner*—Robert A. Wax
*Assistant Examiner*—Suzanne M. (Mayer) Noakes
(74) *Attorney, Agent, or Firm*—Foley & Lardner LLP

(57) ABSTRACT

The present invention provides an antifreeze protein, wherein thermal hysteresis activity and ice recrystallization inhibitory activity are artificially improved. The antifreeze protein is multimerized using a polypeptide linker to improve the thermal hysteresis and ice nuclei growth inhibitory effects in low concentrations.

7 Claims, 14 Drawing Sheets

Fig. 1

CONSTITUTION OF RD3 NCNC

PRIMARY STRUCTURE OF RD3 NCNC

N-domain
Met-Asn-Lys-Ala-Ser-Val-Val-Ala-Asn-Gln-Leu-Ile-Pro-Ile-Asn-Thr-Ala-Leu-Thr-Leu-
Ile-Met-Met-Lys-Ala-Glu-Val-Val-Thr-Pro-Met-Gly-Ile-Pro-Ala-Glu-Glu-Ile-Pro-Asn-
Leu-Val-Gly-Met-Gln-Val-Asn-Arg-Ala-Val-Pro-Leu-Gly-Thr-Thr-Leu-Met-Pro-Asp-Met-
           linker                                    C-domain
Val-Lys-Asn-Tyr-Glu-Asp-Gly-Thr-Thr-Ser-Pro-Gly-Leu-Lys-Ser-Val-Val-Ala-Asn-Gln-
Leu-Ile-Pro-Ile-Asn-Thr-Ala-Leu-Thr-Leu-Val-Met-Met-Lys-Ala-Glu-Glu-Val-Ser-Pro-
Lys-Gly-Ile-Pro-Ser-Glu-Glu-Ile-Ser-Lys-Leu-Val-Gly-Met-Gln-Val-Asn-Arg-Ala-Val-
                                                    linker
Tyr-Leu-Asp-Gln-Thr-Leu-Met-Pro-Asp-Met-Val-Lys-Asn-Tyr-Glu-Asp-Gly-Thr-Thr-Ser-
           N-domain
Pro-Gly-Leu-Lys-Ser-Val-Val-Ala-Asn-Gln-Leu-Ile-Pro-Ile-Asn-Thr-Ala-Leu-Thr-Leu-
Ile-Met-Met-Lys-Ala-Glu-Val-Val-Thr-Pro-Met-Gly-Ile-Pro-Ala-Glu-Glu-Ile-Pro-Asn-
Leu-Val-Gly-Met-Gln-Val-Asn-Arg-Ala-Val-Pro-Leu-Gly-Thr-Thr-Leu-Met-Pro-Asp-Met-
           linker                                    C-domain
Val-Lys-Asn-Tyr-Glu-Asp-Gly-Thr-Thr-Ser-Pro-Gly-Leu-Lys-Ser-Val-Val-Ala-Asn-Gln-
Leu-Ile-Pro-Ile-Asn-Thr-Ala-Leu-Thr-Leu-Val-Met-Met-Lys-Ala-Glu-Glu-Val-Ser-Pro-
Lys-Gly-Ile-Pro-Ser-Glu-Glu-Ile-Ser-Lys-Leu-Val-Gly-Met-Gln-Val-Asn-Arg-Ala-Val-
Tyr-Leu-Asp-Gln-Thr-Leu-Met-Pro-Asp-Met-Val-Lys-Asn-Tyr-Glu

Fig. 2

CONSTITUTION OF RD3 NCC

PRIMARY STRUCTURE OF RD3 NCC

N-domain
Met-Asn-Lys-Ala-Ser-Val-Val-Ala-Asn-Gln-Leu-Ile-Pro-Ile-Asn-Thr-Ala-Leu-Thr-Leu-
Ile-Met-Met-Lys-Ala-Glu-Val-Val-Thr-Pro-Met-Gly-Ile-Pro-Ala-Glu-Glu-Ile-Pro-Asn-
Leu-Val-Gly-Met-Gln-Val-Asn-Arg-Ala-Val-Pro-Leu-Gly-Thr-Thr-Leu-Met-Pro-Asp-Met-
           linker                                    C-domain
Val-Lys-Asn-Tyr-Glu-Asp-Gly-Thr-Thr-Ser-Pro-Gly-Leu-Lys-Ser-Val-Val-Ala-Asn-Gln-
Leu-Ile-Pro-Ile-Asn-Thr-Ala-Leu-Thr-Leu-Val-Met-Met-Lys-Ala-Glu-Glu-Val-Ser-Pro-
Lys-Gly-Ile-Pro-Ser-Glu-Glu-Ile-Ser-Lys-Leu-Val-Gly-Met-Gln-Val-Asn-Arg-Ala-Val-
                                                                    linker
Tyr-Leu-Asp-Gln-Thr-Leu-Met-Pro-Asp-Met-Val-Lys-Asn-Tyr-Glu-Asp-Gly-Thr-Thr-Ser-
        C-domain
Pro-Gly-Leu-Lys-Ser-Val-Val-Ala-Asn-Gln-Leu-Ile-Pro-Ile-Asn-Thr-Ala-Leu-Thr-Leu-
Val-Met-Met-Lys-Ala-Glu-Glu-Val-Ser-Pro-Lys-Gly-Ile-Pro-Ser-Glu-Glu-Ile-Ser-Lys-
Leu-Val-Gly-Met-Gln-Val-Asn-Arg-Ala-Val-Tyr-Leu-Asp-Gln-Thr-Leu-Met-Pro-Asp-Met-
Val-Lys-Asn-Tyr-Glu

Fig. 7

A. SEQUENCE OF RD3 NCNC SENSE STRAND DETERMINED BY DNA SEQUENCING

```
                         ←---- N-domain ----
AATAATTTTG TTTAACTTTA AGAAGGAGAT ATATACATAT GAATAAAGCT TCCGTTGTTG    60

CTAACCAGCT GATCCCGATC AACACCGCTC TGACCCTGAT CATGATGAAA GCTGAAGTTG   120

TTACCCCGAT GGGTATCCCG GCTGAAGAAA TCCCGAACCT GGTTGGTATG CAGGTTAACC   180
                                                        →←
GTGCTGTTCC GCTGGGTACC ACCCTGATGC CGGACATGGT TAAAAACTAC GAAGACGGCA   240
-- linker -----------→ ←---- C-domain ---------
CCACCTCTCC GGGTCTGAAA TCCGTTGTTG CTAACCAGCT GATCCCGATC AACACCGCTC   300

TGACCCTGGT TATGATGAAA GCTGAAGAAG TTTCCCCGAA AGGTATCCCG TCCGAAGAAA   360

TCTCCAAACT GGTTGGTATG CAGGTTAACC GTGCTGTTTA CCTGGACCAG ACCCTGATGC   420
                     →←--------- linker --------→ ←--------
CGGACATGGT TAAAAACTAC GAAGACGGCA CCACCTCCCC GGGTCTGAAA TCCGTTGTTG   480
- N-domain ----------------------------------------------------
CTAACCAGCT GATCCCGATC AACACCGCTC TGACCCTGAT CATGATGAAA GCTGAAGTTG   540

TTACCCCGAT GGGTATCCCG GCTGAAGAAA TCCCGAACCT GGTTGGTATG CAGGTTAACC   600
------------------------------------------------------→
GTGCTGTTCC GCTGGGTACC ACCCTGATGC CGGACATGGT TAAAAACTAC             650
```

B. SEQUENCE OF RD3 NCNC ANTISENSE STRAND DETERMINED BY DNA SEQUENCING

```
CTCAGTGGTG GTGGTGGTGG TGCTCGAGTG CGGCCGCAAG CTTGTCGACG GAGCTCGAAT    60
END←------ C-domain -------------------------------------------
TCGGATCCCT ATTCGTAGTT TTTAACCATG TCCGGCATCA GGGTCTGGTC CAGGTAAACA   120

GCACGGTTAA CCTGCATACC AACCAGTTTG GAGATTTCTT CGGACGGGAT ACCTTTCGGG   180

GAAACTTCTT CAGCTTTCAT CATAACCAGG GTCAGAGCGG TGTTGATCGG GATCAGCTGG   240
              →←----------- linker -----------→ ←---- N-domain ---
TTAGCAACAA CGGATTTCAG ACCCGGAGAG GTGGTGCCGT CTTCGTAGTT TTTAACCATG   300

TCCGGCATCA GGGTGGTACC CAGCGGAACA GCACGGTTAA CCTGCATACC AACCAGGTTC   360

GGGATTTCTT CAGCCGGGAT ACCCATCGGG GTAACAACTT CAGCTTTCAT CATGATCAGG   420
                                               →←------ linker ------
GTCAGAGCGG TGTTGATCGG GATCAGCTGG TTAGCAACAA CGGATTTCAG ACCCGGGGAG   480
------→ ←------ C-domain -------
GTGGTGCCGT CTTCGTAGTT TTTAACCATG TCCGGCATCA GGGTCTGGTC CAGGTAAACA   540

GCACGGTTAA CCTGCATACC AACCAGTTTG GAGATTTCTT CGGACGGGAT ACCTTTCGGG   600

GAAACTTCTT CAGCTTTCAT CATAACCAGG GTCAGAGCGG TGTTGATCGG GATCAGCTGG   660
                   →←linker
TTAGCAACAA CGGATTT                                                  677
```

Fig. 8

A. SEQUENCE OF RD3 NCC SENSE STRAND DETERMINED BY DNA SEQUENCING

```
                         ←―――― N-domain ――――
TTCCTCTNAA AATTTTGTTA ACTTTAGAAG GAGATTCATA TGAATAAAGC TTCCGTTGTT    60

GCTAACCAGC TGATCCCGAT CAACACCGCT CTGACCCTGA TCATGATGAA AGCTGAAGTT   120

GTTACCCCGA TGGGTATCCC GGCTGAAGAA ATCCCGAACC TGGTTGGTAT GCAGGTTAAC   180
                                                     ――――→←――――
CGTGCTGTTC CGCTGGGTAC CACCCTGATG CCGGACATGG TTAAAAACTA CGAAGACGGC   240
―― linker ――――――――→←―― C-domain ――――
ACCACCTCTC CGGGTCTGAA ATCCGTTGTT GCTAACCAGC TGATCCCGAT CAACACCGCT   300

CTGACCCTGG TTATGATGAA AGCTGAAGAA GTTTCCCCGA AAGGTATCCC GTCCGAAGAA   360

ATCTCCAAAC TGGTTGGTAT GCAGGTTAAC CGTGCTGTTT ACCTGGACCA GACCCTGATG   420
                                      ――――→←―――― linker ―――――→←――
CCGGACATGG TTAAAAACTA CGAAGACGGC ACCACCTCCC CGGGTCTGAA ATCCGTTGTT   480
―― C-domain ――――――――――――――――――――――――――――――――――
GCTAACCAGC TGATCCCGAT CAACACCGCT CTGACCCTGG TTATGATGAA AGCTGAAGAA   540

GTTTCCCCGA AAGGTATCCC GTCCGAAGAA ATCTCCAAAC TGGTTGGTAT GCAGGTTAAC   600
                                                         ――→END
CGTGCTGTTT ACCTGGACCA GACCCTGATG CCGGACATGG TTAAAAACTA CGAATAGGGA   660

TCCGAATTCG AGCTCCGTCG ACAAGCTTGC GGC                                693
```

B. SEQUENCE OF RD3 NCC ANTISENSE STRAND DETERMINED BY DNA SEQUENCING

```
GCGGCNNTCA CTTCNTTCGG GCTTTGTTAG CAGCCGGANC TCAGTGGTGG TGGTGGTGGT    60
                                              END←――――――――
GCTCGAGTGC GGCCGCAAGC TTGTCGACGG AGCTCGAATT CGGATCCCTAT TCGTAGTTT   120
―― C-domain ――――――――――――
TTAACCATGT CCGGCATCAG GGTCTGGTCC AGGTAAACAG CACGGTTAACC TGCATACCA   180

ACCAGTTTGG AGATTTCTTC GGACGGGATA CCTTTCGGGG AAACTTCTTCA GCTTTCATC   240
                                                      ――――→←――――
ATAACCAGGG TCAGAGCGGT GTTGATCGGG ATCAGCTGGT TAGCAACAACG GATTTCAGA   300
―― linker ―――――→←―――――― C-domain ――――
CCCGGGGAGG TGGTGCCGTC TTCGTAGTTT TTAACCATGT CCGGCATCANG GTCTGGTCC   360

AGGTAAACAG CACGGTTAAC CTGCATACCA ACCAGTTTGG AGATTTCTTCG GACGGGATA   420

CCTTTCGGGG AAACTTCTTC AGCTTTCATC ATAACCAGGG TCAGAGCGGTG TTGATCGGG   480
       ――――→←―――――― linker ――――→←――
ATCAGCTGGT TAGCANCAAC GGATTTCAGA CCCGGAGAGG TGGTGCCGTCT TCGTAGTTT   540
―― N-domain ―――――――――――――――
TTAACCATGT CCGGCATCAG GGTGGTACCC AGCGGAACA                          579
```

\* N represents an undetermined nucleotide

SEQUENCE LISTING

<160> NUMBER OF SEQ ID NOS: 20

<210> SEQ ID NO 1
<211> LENGTH: 828
<212> TYPE: DNA
<213> ORGANISM: Artificial Sequence
<220> FEATURE:
<223> OTHER INFORMATION: Description of Artificial Sequence: DNA
      sequence of RD3 NCNC comprised of tetramerized Type III
      AFPs connected by three 9-residue peptides
<220> FEATURE:
<221> NAME/KEY: CDS
<222> LOCATION: (1)..(825)

<400> SEQUENCE: 1

```
atg aat aaa gct tcc gtt gtt gct aac cag ctg atc ccg atc aac acc       48
Met Asn Lys Ala Ser Val Val Ala Asn Gln Leu Ile Pro Ile Asn Thr
 1               5                  10                  15 gct ctg acc ctg atc atg atg aaa gct gaa gtt gtt acc ccg atg ggt       96
Ala Leu Thr Leu Ile Met Met Lys Ala Glu Val Val Thr Pro Met Gly
             20                  25                  30 atc ccg gct gaa gaa atc ccg aac ctg gtt ggt atg cag gtt aac cgt      144
Ile Pro Ala Glu Glu Ile Pro Asn Leu Val Gly Met Gln Val Asn Arg
         35                  40                  45 gct gtt ccg ctg ggt acc acc ctg atg ccg gac atg gtt aaa aac tac      192
Ala Val Pro Leu Gly Thr Thr Leu Met Pro Asp Met Val Lys Asn Tyr
     50                  55                  60 gaa gac ggc acc acc tct ccg ggt ctg aaa tcc gtt gtt gct aac cag      240
Glu Asp Gly Thr Thr Ser Pro Gly Leu Lys Ser Val Val Ala Asn Gln
 65                  70                  75                  80 ctg atc ccg atc aac acc gct ctg acc ctg gtt atg atg aaa gct gaa      288
Leu Ile Pro Ile Asn Thr Ala Leu Thr Leu Val Met Met Lys Ala Glu
                 85                  90                  95 gaa gtt tcc ccg aaa ggt atc ccg tcc gaa gaa atc tcc aaa ctg gtt      336
Glu Val Ser Pro Lys Gly Ile Pro Ser Glu Glu Ile Ser Lys Leu Val
            100                 105                 110 ggt atg cag gtt aac cgt gct gtt tac ctg gac cag acc ctg atg ccg      384
Gly Met Gln Val Asn Arg Ala Val Tyr Leu Asp Gln Thr Leu Met Pro
        115                 120                 125 gac atg gtt aaa aac tac gaa gac ggc acc acc tcc ccg ggt ctg aaa      432
Asp Met Val Lys Asn Tyr Glu Asp Gly Thr Thr Ser Pro Gly Leu Lys
    130                 135                 140 tcc gtt gtt gct aac cag ctg atc ccg atc aac acc gct ctg acc ctg      480
Ser Val Val Ala Asn Gln Leu Ile Pro Ile Asn Thr Ala Leu Thr Leu
145                 150                 155                 160 atc atg atg aaa gct gaa gtt gtt acc ccg atg ggt atc ccg gct gaa      528
Ile Met Met Lys Ala Glu Val Val Thr Pro Met Gly Ile Pro Ala Glu
                165                 170                 175 gaa atc ccg aac ctg gtt ggt atg cag gtt aac cgt gct gtt ccg ctg      576
Glu Ile Pro Asn Leu Val Gly Met Gln Val Asn Arg Ala Val Pro Leu
            180                 185                 190 ggt acc acc ctg atg ccg gac atg gtt aaa aac tac gaa gac ggc acc      624
Gly Thr Thr Leu Met Pro Asp Met Val Lys Asn Tyr Glu Asp Gly Thr
        195                 200                 205 acc tct ccg ggt ctg aaa tcc gtt gtt gct aac cag ctg atc ccg atc      672
Thr Ser Pro Gly Leu Lys Ser Val Val Ala Asn Gln Leu Ile Pro Ile
    210                 215                 220 aac acc gct ctg acc ctg gtt atg atg aaa gct gaa gaa gtt tcc ccg      720
Asn Thr Ala Leu Thr Leu Val Met Met Lys Ala Glu Glu Val Ser Pro
225                 230                 235                 240
```

-continued

```
aaa ggt atc ccg tcc gaa gaa atc tcc aaa ctg gtt ggt atg cag gtt       768
Lys Gly Ile Pro Ser Glu Glu Ile Ser Lys Leu Val Gly Met Gln Val
            245                 250                 255 aac cgt gct gtt tac ctg gac cag acc ctg atg ccg gac atg gtt aaa       816
Asn Arg Ala Val Tyr Leu Asp Gln Thr Leu Met Pro Asp Met Val Lys
            260                 265                 270 aac tac gaa tag                                                       828
Asn Tyr Glu
        275
```

<210> SEQ ID NO 2
<211> LENGTH: 275
<212> TYPE: PRT
<213> ORGANISM: Artificial Sequence
<220> FEATURE:
<223> OTHER INFORMATION: Description of Artificial Sequence: Amino acid
      sequence of RD3 NCNC comprised of tetramerized Type III
      AFPs connected by three 9-residue peptides

<400> SEQUENCE: 2

```
Met Asn Lys Ala Ser Val Val Ala Asn Gln Leu Ile Pro Ile Asn Thr
  1               5                  10                  15

Ala Leu Thr Leu Ile Met Met Lys Ala Glu Val Val Thr Pro Met Gly
             20                  25                  30

Ile Pro Ala Glu Glu Ile Pro Asn Leu Val Gly Met Gln Val Asn Arg
         35                  40                  45

Ala Val Pro Leu Gly Thr Thr Leu Met Pro Asp Met Val Lys Asn Tyr
     50                  55                  60

Glu Asp Gly Thr Thr Ser Pro Gly Leu Lys Ser Val Val Ala Asn Gln
 65                  70                  75                  80

Leu Ile Pro Ile Asn Thr Ala Leu Thr Leu Val Met Met Lys Ala Glu
                 85                  90                  95

Glu Val Ser Pro Lys Gly Ile Pro Ser Glu Glu Ile Ser Lys Leu Val
            100                 105                 110

Gly Met Gln Val Asn Arg Ala Val Tyr Leu Asp Gln Thr Leu Met Pro
        115                 120                 125

Asp Met Val Lys Asn Tyr Glu Asp Gly Thr Thr Ser Pro Gly Leu Lys
    130                 135                 140

Ser Val Val Ala Asn Gln Leu Ile Pro Ile Asn Thr Ala Leu Thr Leu
145                 150                 155                 160

Ile Met Met Lys Ala Glu Val Val Thr Pro Met Gly Ile Pro Ala Glu
                165                 170                 175

Glu Ile Pro Asn Leu Val Gly Met Gln Val Asn Arg Ala Val Pro Leu
            180                 185                 190

Gly Thr Thr Leu Met Pro Asp Met Val Lys Asn Tyr Glu Asp Gly Thr
        195                 200                 205

Thr Ser Pro Gly Leu Lys Ser Val Val Ala Asn Gln Leu Ile Pro Ile
    210                 215                 220

Asn Thr Ala Leu Thr Leu Val Met Met Lys Ala Glu Val Ser Pro
225                 230                 235                 240

Lys Gly Ile Pro Ser Glu Glu Ile Ser Lys Leu Val Gly Met Gln Val
                245                 250                 255

Asn Arg Ala Val Tyr Leu Asp Gln Thr Leu Met Pro Asp Met Val Lys
            260                 265                 270

Asn Tyr Glu
        275
```

<210> SEQ ID NO 3
<211> LENGTH: 618
<212> TYPE: DNA
<213> ORGANISM: Artificial Sequence
<220> FEATURE:
<223> OTHER INFORMATION: Description of Artificial Sequence: DNA
sequence of RD3 NCC comprised of trimerized Type III AFPs
connected by two 9-residue peptides
<220> FEATURE:
<221> NAME/KEY: CDS
<222> LOCATION: (1)..(615)

<400> SEQUENCE: 3

| atg aat aaa gct tcc gtt gtt gct aac cag ctg atc ccg atg aac acc | 48 |
| Met Asn Lys Ala Ser Val Val Ala Asn Gln Leu Ile Pro Met Asn Thr | |
| 1               5                   10                  15 | |

| gct ctg acc ctg atc atg atg aaa gct gaa gtt gtt acc ccg atg ggt | 96 |
| Ala Leu Thr Leu Ile Met Met Lys Ala Glu Val Val Thr Pro Met Gly | |
|             20                  25                  30 | |

| atc ccg gct gaa gaa atc ccg aac ctg gtt ggt atg cag gtt aac cgt | 144 |
| Ile Pro Ala Glu Glu Ile Pro Asn Leu Val Gly Met Gln Val Asn Arg | |
|         35                  40                  45 | |

| gct gtt ccg ctg ggt acc acc ctg atg ccg gac atg gtt aaa aac tac | 192 |
| Ala Val Pro Leu Gly Thr Thr Leu Met Pro Asp Met Val Lys Asn Tyr | |
|     50                  55                  60 | |

| gaa gac ggc acc acc tct ccg ggt ctg aaa tcc gtt gtt gct aac cag | 240 |
| Glu Asp Gly Thr Thr Ser Pro Gly Leu Lys Ser Val Val Ala Asn Gln | |
| 65                  70                  75                  80 | |

| ctg atc ccg atc aac acc gct ctg acc ctg gtt atg atg aaa gct gaa | 288 |
| Leu Ile Pro Ile Asn Thr Ala Leu Thr Leu Val Met Met Lys Ala Glu | |
|                 85                  90                  95 | |

| gaa gtt tcc ccg aaa ggt atc ccg tcc gaa gaa atc tcc aaa ctg gtt | 336 |
| Glu Val Ser Pro Lys Gly Ile Pro Ser Glu Glu Ile Ser Lys Leu Val | |
|             100                 105                 110 | |

| ggt atg cag gtt aac cgt gct gtt tac ctg gac cag acc ctg atg ccg | 384 |
| Gly Met Gln Val Asn Arg Ala Val Tyr Leu Asp Gln Thr Leu Met Pro | |
|         115                 120                 125 | |

| gac atg gtt aaa aac tac gaa gac ggc acc acc tcc ccg ggt ctg aaa | 432 |
| Asp Met Val Lys Asn Tyr Glu Asp Gly Thr Thr Ser Pro Gly Leu Lys | |
|     130                 135                 140 | |

| tcc gtt gtt gct aac cag ctg atc ccg atc aac acc gct ctg acc ctg | 480 |
| Ser Val Val Ala Asn Gln Leu Ile Pro Ile Asn Thr Ala Leu Thr Leu | |
| 145                 150                 155                 160 | |

| gtt atg atg aaa gct gaa gaa gtt tcc ccg aaa ggt atc ccg tcc gaa | 528 |
| Val Met Met Lys Ala Glu Glu Val Ser Pro Lys Gly Ile Pro Ser Glu | |
|                 165                 170                 175 | |

| gaa atc tcc aaa ctg gtt ggt atg cag gtt aac cgt gct gtt tac ctg | 576 |
| Glu Ile Ser Lys Leu Val Gly Met Gln Val Asn Arg Ala Val Tyr Leu | |
|             180                 185                 190 | |

| gac cag acc ctg atg ccg gac atg gtt aaa aac tac gaa tag | 618 |
| Asp Gln Thr Leu Met Pro Asp Met Val Lys Asn Tyr Glu | |
|         195                 200                 205 | |

<210> SEQ ID NO 4
<211> LENGTH: 205
<212> TYPE: PRT
<213> ORGANISM: Artificial Sequence
<220> FEATURE:
<223> OTHER INFORMATION: Description of Artificial Sequence: Amino acid
sequence of RD3 NCC comprised of trimerized Type III AFPs
connected by two 9-residue peptides

<400> SEQUENCE: 4

Met Asn Lys Ala Ser Val Val Ala Asn Gln Leu Ile Pro Met Asn Thr

```
            1               5              10              15
          Ala Leu Thr Leu Ile Met Met Lys Ala Glu Val Val Thr Pro Met Gly
                          20                  25                  30

Ile Pro Ala Glu Glu Ile Pro Asn Leu Val Gly Met Gln Val Asn Arg
                          35                  40                  45

Ala Val Pro Leu Gly Thr Thr Leu Met Pro Asp Met Val Lys Asn Tyr
                          50                  55                  60

Glu Asp Gly Thr Thr Ser Pro Gly Leu Lys Ser Val Val Ala Asn Gln
           65                  70                  75                  80

Leu Ile Pro Ile Asn Thr Ala Leu Thr Leu Val Met Met Lys Ala Glu
                          85                  90                  95

Glu Val Ser Pro Lys Gly Ile Pro Ser Glu Glu Ile Ser Lys Leu Val
                         100                 105                 110

Gly Met Gln Val Asn Arg Ala Val Tyr Leu Asp Gln Thr Leu Met Pro
                         115                 120                 125

Asp Met Val Lys Asn Tyr Glu Asp Gly Thr Thr Ser Pro Gly Leu Lys
                         130                 135                 140

Ser Val Val Ala Asn Gln Leu Ile Pro Ile Asn Thr Ala Leu Thr Leu
          145                 150                 155                 160

Val Met Met Lys Ala Glu Glu Val Ser Pro Lys Gly Ile Pro Ser Glu
                         165                 170                 175

Glu Ile Ser Lys Leu Val Gly Met Gln Val Asn Arg Ala Val Tyr Leu
                         180                 185                 190

Asp Gln Thr Leu Met Pro Asp Met Val Lys Asn Tyr Glu
                         195                 200                 205

<210> SEQ ID NO 5
<211> LENGTH: 408
<212> TYPE: DNA
<213> ORGANISM: Artificial Sequence
<220> FEATURE:
<223> OTHER INFORMATION: Description of Artificial Sequence: DNA
      sequence of RD3 optimized for over expression in Escherichia
      coli
<220> FEATURE:
<221> NAME/KEY: CDS
<222> LOCATION: (1)..(405)

<400> SEQUENCE: 5 atg aat aaa gct tcc gtt gtt gct aac cag ctg atc ccg atc aac acc       48
Met Asn Lys Ala Ser Val Val Ala Asn Gln Leu Ile Pro Ile Asn Thr
  1               5                  10                  15 gct ctg acc ctg atc atg atg aaa gct gaa gtt gtt acc ccg atg ggt       96
Ala Leu Thr Leu Ile Met Met Lys Ala Glu Val Val Thr Pro Met Gly
                 20                  25                  30 atc ccg gct gaa gaa atc ccg aac ctg gtt ggt atg cag gtt aac cgt      144
Ile Pro Ala Glu Glu Ile Pro Asn Leu Val Gly Met Gln Val Asn Arg
             35                  40                  45 gct gtt ccg ctg ggt acc acc ctg atg ccg gac atg gtt aaa aac tac      192
Ala Val Pro Leu Gly Thr Thr Leu Met Pro Asp Met Val Lys Asn Tyr
         50                  55                  60 gaa gac ggt acc acc tcc ccg ggt ctg aaa tcc gtt gtt gct aac cag      240
Glu Asp Gly Thr Thr Ser Pro Gly Leu Lys Ser Val Val Ala Asn Gln
 65                  70                  75                  80 ctg atc ccg atc aac acc gct ctg acc ctg gtt atg atg aaa gct gaa      288
Leu Ile Pro Ile Asn Thr Ala Leu Thr Leu Val Met Met Lys Ala Glu
                 85                  90                  95 gaa gtt tcc ccg aaa ggt atc ccg tcc gaa gaa atc tcc aaa ctg gtt      336
Glu Val Ser Pro Lys Gly Ile Pro Ser Glu Glu Ile Ser Lys Leu Val
```

```
                100             105             110
ggt atg cag gtt aac cgt gct gtt tac ctg gac cag acc ctg atg ccg      384
Gly Met Gln Val Asn Arg Ala Val Tyr Leu Asp Gln Thr Leu Met Pro
        115             120             125 gac atg gtt aaa aac tac gaa tag                                      408
Asp Met Val Lys Asn Tyr Glu
    130             135
```

<210> SEQ ID NO 6
<211> LENGTH: 135
<212> TYPE: PRT
<213> ORGANISM: Lycodichthys dearborni
<220> FEATURE:
<223> OTHER INFORMATION: Description of Artificial Sequence: Amino acid
      sequence of RD3

<400> SEQUENCE: 6

```
Met Asn Lys Ala Ser Val Val Ala Asn Gln Leu Ile Pro Ile Asn Thr
 1               5                  10                  15

Ala Leu Thr Leu Ile Met Met Lys Ala Glu Val Val Thr Pro Met Gly
                20                  25                  30

Ile Pro Ala Glu Glu Ile Pro Asn Leu Val Gly Met Gln Val Asn Arg
            35                  40                  45

Ala Val Pro Leu Gly Thr Thr Leu Met Pro Asp Met Val Lys Asn Tyr
        50                  55                  60

Glu Asp Gly Thr Thr Ser Pro Gly Leu Lys Ser Val Val Ala Asn Gln
 65                 70                  75                  80

Leu Ile Pro Ile Asn Thr Ala Leu Thr Leu Val Met Met Lys Ala Glu
                85                  90                  95

Glu Val Ser Pro Lys Gly Ile Pro Ser Glu Glu Ile Ser Lys Leu Val
                100                 105                 110

Gly Met Gln Val Asn Arg Ala Val Tyr Leu Asp Gln Thr Leu Met Pro
            115                 120                 125

Asp Met Val Lys Asn Tyr Glu
        130             135
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: PCR primer
      for the construction of recombinant RD3 without Kpn I
      and Sma I restriction enzyme sites in linker
      region

<400> SEQUENCE: 7
gagctgcagt taactttaag                                                20

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: PCR primer
      for the construction of recombinant RD3 without Kpn I
      and Sma I restriction enzyme sites in linker
      region

<400> SEQUENCE: 8
acccggagag gtggtgccgt cttcgtagtt ttta                                34

```
<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: PCR primer
      for the construction of recombinant RD3 without Kpn I
      and Sma I restriction enzyme sites in linker
      region

<400> SEQUENCE: 9
agacggcacc acctctccgg gtctgaaatc cgttg                          35

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: PCR primer
      for the construction of recombinant RD3 without Kpn I
      and Sma I restriction enzyme sites in linker
      region

<400> SEQUENCE: 10
ttcgagctcc accgcggtgg cg                                        22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR primer
      for the construction of RD3 NC1

<400> SEQUENCE: 11
gagctgcagt taactttaag                                           20

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: PCR primer
      for the construction of RD3 NC1

<400> SEQUENCE: 12
gtcccccggg gaggtggtgc cgtcttcgta gttttttaacc atgtccggca tcagggtctg   60

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: PCR primer
      for the construction of RD3 1N

<400> SEQUENCE: 13
ggaactgcag cccgggtctg aaatccgttg ttgctaacca g                   41

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR primer
      for the construction of RD3 1N

<400> SEQUENCE: 14
```

-continued cgcggatcct attcgtagtt tttaaccatg                                              30

<210> SEQ ID NO 15
<211> LENGTH: 579
<212> TYPE: DNA
<213> ORGANISM: Artificial Sequence
<220> FEATURE:
<223> OTHER INFORMATION: Description of Artificial Sequence: DNA
      sequence of antisense RD3 NCNC
<220> FEATURE:
<221> NAME/KEY: modified_base
<222> LOCATION: (6)..(7)
<223> OTHER INFORMATION: a, c, g, t, unknown or other
<220> FEATURE:
<221> NAME/KEY: modified_base
<222> LOCATION: (15)
<223> OTHER INFORMATION: a, c, g, t, unknown or other
<220> FEATURE:
<221> NAME/KEY: modified_base
<222> LOCATION: (39)
<223> OTHER INFORMATION: a, c, g, t, unknown or other
<220> FEATURE:
<221> NAME/KEY: modified_base
<222> LOCATION: (350)
<223> OTHER INFORMATION: a, c, g, t, unknown or other
<220> FEATURE:
<221> NAME/KEY: modified_base
<222> LOCATION: (496)
<223> OTHER INFORMATION: a, c, g, t, unknown or other

<400> SEQUENCE: 15
gcgccnntca cttcnttcgg gctttgttag cagccgganc tcagtggtgg tggtggtggt    60
gctcgagtgc ggccgcaagc ttgtcgacgg agctcgaatt cggatcccta ttcgtagttt   120
ttaaccatgt ccggcatcag ggtctggtcc aggtaaacag cacggttaac ctgcatacca   180
accagtttgg agatttcttc ggacgggata cctttcgggg aaacttcttc agctttcatc   240
ataaccaggg tcagagcggt gttgatcggg atcagctggt tagcaacaac ggatttcaga   300
cccggggagg tggtgccgtc ttcgtagttt ttaaccatgt ccggcatcan ggtctggtcc   360
aggtaaacag cacggttaac ctgcatacca accagtttgg agatttcttc ggacgggata   420
cctttcgggg aaacttcttc agctttcatc ataaccaggg tcagagcggt gttgatcggg   480
atcagctggt tagcancaac ggatttcaga cccggagagg tggtgccgtc ttcgtagttt   540
ttaaccatgt ccggcatcag ggtggtaccc agcggaaca                          579

<210> SEQ ID NO 16
<211> LENGTH: 677
<212> TYPE: DNA
<213> ORGANISM: Artificial Sequence
<220> FEATURE:
<223> OTHER INFORMATION: Description of Artificial Sequence: DNA
      sequence of antisense RD3 NCC

<400> SEQUENCE: 16
ctcagtggtg gtggtggtgg tgctcgagtg cggccgcaag cttgtcgacg gagctcgaat    60
tcggatccct attcgtagtt tttaaccatg tccggcatca gggtctggtc caggtaaaca   120
gcacggttaa cctgcatacc aaccagtttg gagatttctt cggacgggat acctttcggg   180
gaaacttctt cagctttcat cataaccagg gtcagagcgg tgttgatcgg gatcagctgg   240
ttagcaacaa cggatttcag acccggagag gtggtgccgt cttcgtagtt tttaaccatg   300
tccggcatca gggtggtacc cagcggaaca gcacggttaa cctgcatacc aaccaggttc   360
gggatttctt cagccgggat acccatcggg gtaacaactt cagctttcat catgatcagg   420
gtcagagcgg tgttgatcgg gatcagctgg ttagcaacaa cggatttcag acccggggag   480

| | |
|---|---|
| gtggtgccgt cttcgtagtt tttaaccatg tccggcatca gggtctggtc caggtaaaca | 540 |
| gcacggttaa cctgcatacc aaccagtttg agatttctt cggacgggat acctttcggg | 600 |
| gaaacttctt cagctttcat cataaccagg gtcagagcgg tgttgatcgg gatcagctgg | 660 |
| ttagcaacaa cggattt | 677 |

<210> SEQ ID NO 17
<211> LENGTH: 650
<212> TYPE: DNA
<213> ORGANISM: Artificial Sequence
<220> FEATURE:
<223> OTHER INFORMATION: Description of Artificial Sequence: DNA
      sequence of RD3 NCNC

<400> SEQUENCE: 17

| | |
|---|---|
| aataattttg tttaacttta agaaggagat atatacatat gaataaagct tccgttgttg | 60 |
| ctaaccagct gatcccgatc aacaccgctc tgaccctgat catgatgaaa gctgaagttg | 120 |
| ttaccccgat gggtatcccg gctgaagaaa tcccgaacct ggttggtatg caggttaacc | 180 |
| gtgctgttcc gctgggtacc accctgatgc cggacatggt taaaaactac gaagacggca | 240 |
| ccacctctcc gggtctgaaa tccgttgttg ctaaccagct gatcccgatc aacaccgctc | 300 |
| tgaccctggt tatgatgaaa gctgaagaag tttccccgaa aggtatcccg tccgaagaaa | 360 |
| tctccaaact ggttggtatg caggttaacc gtgctgttta cctggaccag accctgatgc | 420 |
| cggacatggt taaaaactac gaagacggca ccacctcccc gggtctgaaa tccgttgttg | 480 |
| ctaaccagct gatcccgatc aacaccgctc tgaccctgat catgatgaaa gctgaagttg | 540 |
| ttaccccgat gggtatcccg gctgaagaaa tcccgaacct ggttggtatg caggttaacc | 600 |
| gtgctgttcc gctgggtacc accctgatgc cggacatggt taaaaactac | 650 |

<210> SEQ ID NO 18
<211> LENGTH: 692
<212> TYPE: DNA
<213> ORGANISM: Artificial Sequence
<220> FEATURE:
<223> OTHER INFORMATION: Description of Artificial Sequence: DNA
      sequence of RD3 NCC
<220> FEATURE:
<221> NAME/KEY: modified_base
<222> LOCATION: (8)
<223> OTHER INFORMATION: a, c, g, t, unknown or other

<400> SEQUENCE: 18

| | |
|---|---|
| ttcctctnaa aattttgtta actttagaag gagattcata tgaataaagc ttccgttgtt | 60 |
| gctaaccagc tgatcccgat caacaccgct ctgaccctga tcatgatgaa agctgaagtt | 120 |
| gttaccccga tgggtatccc ggctgaagaa atcccgaacc tggttggtat gcaggttaac | 180 |
| cgtgctgttc cgctgggtac caccctgatg ccggacatgg ttaaaaacta cgaagacggc | 240 |
| accacctctc cgggtctgaa atccgttgtt gctaaccagc tgatcccgat caacaccgct | 300 |
| ctgaccctgg ttatgatgaa agctgaagaa gtttccccga aggtatccc gtccgaagaa | 360 |
| atctccaaac tggttggtat gcaggttaac cgtgctgttt acctggacca gaccctgatg | 420 |
| ccggacatgg ttaaaaacta cgaagacggc accacctccc cgggtctgaa atccgttgtt | 480 |
| gctaaccagc tgatcccgat caacaccgct ctgaccctgg ttatgatgaa agctgaagaa | 540 |
| gtttccccga aggtatccc gtccgaagaa atctccaaac tggttggtat gcaggttaac | 600 |
| cgtgctgttt acctggacca gaccctgatg ccggacatgg ttaaaaacta cgaatavggga | 660 |

```
tccgaattcg agctccgtcg agagcttgcg gc                                        692
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 19

Asp Gly Thr Thr Ser Pro Gly Leu Lys
  1               5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)
<223> OTHER INFORMATION: Variable amino acid

<400> SEQUENCE: 20

Thr Cys Thr Xaa Ser Xaa Xaa Cys Xaa Xaa Ala Xaa
  1               5                  10

MULTIMERIZED HIGHLY FUNCTIONAL ANTIFREEZE PROTEIN

BACKGROUND OF THE INVENTION

1. Field of the Invention

The present invention relates to a novel protein prepared by modifying a native antifreeze protein, and more particularly to a multimerized antifreeze protein, which exhibits excellent ice nuclei growth inhibition at low concentrations and is used as an inhibitor for ice recrystallization and as a cryopreservative, a method for producing the same, and DNA encoding a multimerized antifreeze protein.

2. Prior Art

Antifreeze peptides and antifreeze proteins (AFPs) generally have properties such as 1) thermal hysteresis, 2) inhibition of ice recrystallization, and 3) modification of ice growth. Accordingly, the use as an additive for ice creams, in which flavor and taste deteriorate due to the recrystallization caused by cold storage, or the use as a cryopreservative for cells and organs has been proposed. In a cooling system, cold storage, or the like using ice slurry, AFPs are expected as effective additives capable of dissolving blocked piping systems caused by ice recrystallization. Up to the present, native antifreeze proteins derived from plants and fishes have been mainly used in attempts to: maintain the quality of frozen foods such as ice creams; protect cells during cryopreservation; and apply for cooling systems, cold storages, or the like.

Antifreeze peptides and antifreeze proteins (AFPs), as described in more detail hereafter, generally have at least one of the following properties: 1) thermal hysteresis; 2) inhibition of ice recrystallization; or 3) modification of ice growth. Thus, the use thereof for maintaining the quality of foods or cells during cryopreservation has been proposed (Marilyn Greffith and K. Vanya Ewart, 1995. *Biotechnology Advance* 13: 375–402.). It has been suggested that these properties of AFP are derived from the phenomenon that binding of AFP to ice surface results in a creating convex ice surface, which energetically unfavorable for water to join the ice lattice.

AFPs have been discovered in many organisms such as fishes, insects, plants, bacteria, and fungi (John Barrett, 2001. Int J Biochem Cell Biol. 33: 105–117). One of the AFPs, which have been extensively researched, is the AFP derived from polar fishes. The fish—into five structural types; AFGP, i.e., an antifreeze glycoprotein derived AFP can be classified, which has a repeated tripeptide motif (Ala-Ala-Thr) with a disaccharide attached to threonine and is approximately 2,600 to 34,000 Da protein; Type I AFP, which is alanine-rich, α-helix protein; Type II AFP, which is cysteine-rich protein and appears to be homolog of the carbohydrate recognition domain of C-type lectins; Type III AFP, which is a small globular protein with a molecular weight of 6,500 to 7,000 Da; and Type IV AFP, which is predicted to be four-helix bundle structure. Fish-derived AFP is known to cause ice nuclei to grow into bipyramidal ice crystals (FIG. 12A), and this mechanism is construed to be as follows.

In general, when ice nuclei appear in an aqueous solution, the ice crystal first grows into a planar hexagon or square plate. The growth in a vertical direction to the plate is approximately 100 times slower than that in a planar direction. In contrast, when an antifreeze protein is present in the aqueous solution, ice crystal growth in the planar direction is inhibited, then the first-formed plate acts as a base surface upon which smaller plates are successively stacked on top of each other in the vertical direction to the base surface, and finally, the plates slowly grow into a bipyramidal ice crystal comprising two pyramidals jointed to each other.

Accordingly, when the body fluid of the fish having an antifreeze protein is cooled to subzero temperature, bipyramidal ice crystals are observed in the body fluid under a microscope. Such bipyramidal ice crystals are generated by the capacity of the antifreeze protein which specifically binds to the 12 equivalent bipyramidal planes of ice crystal. In the freezing temperature ranging at 0° C. or below, microscopically, the antifreeze proteins in the body fluid generate infinite number of bipyramidal ice crystals, which do not bind to each other. This is macroscopically observed as a non-freezing phenomenon (antifreeze activities) of specimens.

In 1995, Xin Wang et al. reported three major Type III AFPs derived from antarctic eel pout, and among them, the AFP designated as RD3 had a sequencecomprising two Type III AFPs (N-domain and C-domain) ligated to each other by a polypeptide linker constituted of nine amino acid residues (Asp-Gly-Thr-Thr-Ser-Pro-Gly-Leu-Lys) (SEQ ID NO: 19) (Xin Wang et al., 1995. Biochim. Biophys. Acta 1247: 163–172). Further, they also reported that RD3 exhibited thermal hysteresis approximately twice as much as that of other Type III AFPs on the molar concentration basis. Kazunori Miura et al. determined the RD3 structure by using NMR and reported that two predicted ice-binding planes of RD3 were located substantially on the same plane (Kazunori Miura et al., 2001, *J. Biol. Chem.* 276: 1304–1310). They also reported that RD3 exhibited thermal hysteresis 6 times as much as that of Type III AFP on the molar concentration basis in low molar concentrations ranging from 0.1 to 0.2 mM. This indicates that RD3 possesses thermal hysteresis activity as much as three times per molecule of Type III AFP in low concentrations.

In the past, quality maintenance of frozen foods such as ice creams and protection of cells during cryopreservation using antifreeze proteins derived from plants and fishes have been mainly attempted, although none has yet been put to practical use. Regardless of the high effectiveness being expected, the practical application thereof for cooling systems, cold storages, and the like, have not been forthcoming because of reasons such as insufficient level of activity and high protein requirements to obtain desired effects.

SUMMARY OF THE INVENTION

The present invention is intended to solve such conventional problems, and an object of the present invention is to improve the antifreeze proteins existing in living organisms and to improve thermal hysteresis, ice recrystallization inhibitory activity, and the like of the antifreeze protein, thereby enhancing its applicability.

In order to improve thermal hysteresis, ice recrystallization inhibitory activity, and the like of the antifreeze protein, site-specific mutagenesis into the antifreeze protein may be carried out. However, it is very difficult to determine the suitable mutagenesis site and the suitable amino acid residues to be substituted.

The present inventors have focused on the structure, Type III AFP-linker-Type III AFP, which has been observed in native RD3. They produced a multimerized antifreeze protein by ligating three or more antifreeze proteins by peptide linkers, and they investigated its antifreeze activities. As a result, it exhibited unexpectedly significant antifreeze activities, and this had led to the completion of the present invention.

More specifically, the present invention relates to the following.

(1) A multimerized antifreeze protein, wherein three or more antifreeze proteins or peptides are ligated by linker peptides.

(2) A protein selected from the group consisting of the following (a) and (b):
(a) a protein comprising an amino acid sequence as shown in SEQ ID NO: 2;
(b) a protein comprising an amino acid sequence as shown in SEQ ID NO: 2 having deletion, substitution, or addition of one or more amino acids and having an antifreeze activity.

(3) A DNA encoding a protein selected from the group consisting of the following (a) and (b):
(a) a protein comprising an amino acid sequence as shown in SEQ ID NO: 2;
(b) a protein comprising an amino acid sequence as shown in SEQ ID NO: 2 having deletion, substitution, or addition of one or more amino acids and having an antifreeze activity.

(4) A DNA comprising the following (a) or (b):
(a) a DNA having a nucleotide sequence as shown in SEQ ID NO: 1;
(b) a DNA which hybridizes to a DNA complementary to a DNA consisting of all or a portion of a nucleotide sequence as shown in SEQ ID NO: 1 under stringent conditions, and which encodes a protein having an antifreeze activity.

(5) A protein selected from the group consisting of the following (a) and (b):
(a) a protein comprising an amino acid sequence as shown in SEQ ID NO: 4;
(b) a protein comprising an amino acid sequence as shown in SEQ ID NO: 4 having deletion, substitution, or addition of one or more amino acids and having an antifreeze activity.

(6) A DNA encoding a protein selected from the group consisting of the following (a) and (b):
(a) a protein comprising an amino acid sequence as shown in SEQ ID NO: 4;
(b) a protein comprising an amino acid sequence as shown in SEQ ID NO: 4 having deletion, substitution, or addition of one or more amino acids and having an antifreeze activity.

(7) A DNA comprising the following (a) or (b):
(a) a DNA having a nucleotide sequence as shown in SEQ ID NO: 3;
(b) a DNA which hybridizes to a DNA complementary to a DNA consisting of all or a portion of a nucleotide sequence as shown in SEQ ID NO: 3 under stringent conditions, and which encodes a protein having an antifreeze activity.

(8) A recombinant vector comprising the DNA according to (4).

(9) A recombinant vector comprising the DNA according to (7).

(10) A transformant having the recombinant vector according to (8).

(11) A transformant having the recombinant vector according to (9).

(12) A method for producing a multimerized antifreeze protein or peptide, wherein the multimerized antifreeze protein according to (1) is synthesized using a peptide synthesizer.

(13) A method for producing a multimerized antifreeze protein, wherein the multimerized antifreeze protein according to (2) is synthesized using a peptide synthesizer.

(14) A method for producing a multimerized antifreeze protein, wherein the multimerized antifreeze protein according to (5) is synthesized using a peptide synthesizer.

(15) A method for producing a multimerized antifreeze protein or peptide, wherein the transformant according to (10) is cultured to obtain the multimerized antifreeze protein or peptide.

(16) A method for producing a multimerized antifreeze protein or peptide, wherein the transformant according to (11) is cultured to obtain the multimerized antifreeze protein or peptide.

BRIEF DESCRIPTION OF DRAWINGS

FIG. 1 shows a constitution of RD3 NCNC and its primary structure (SEQ ID NO: 2).

FIG. 2 shows a constitution of RD3 NCC and its primary structure (SEQ ID NO: 4).

FIG. 7 shows a result of analysis of the DNA sequence of pETRD3NCNC (SEQ ID NO: 17 and 16, respectively in order of appearance).

FIG. 8 shows a result of analysis of the DNA sequence of pETRD3NCC (SEQ ID NO: 18 and 15, respectively in order of appearance).

DETAILED DESCRIPTION OF THE INVENTION

Figure 3:
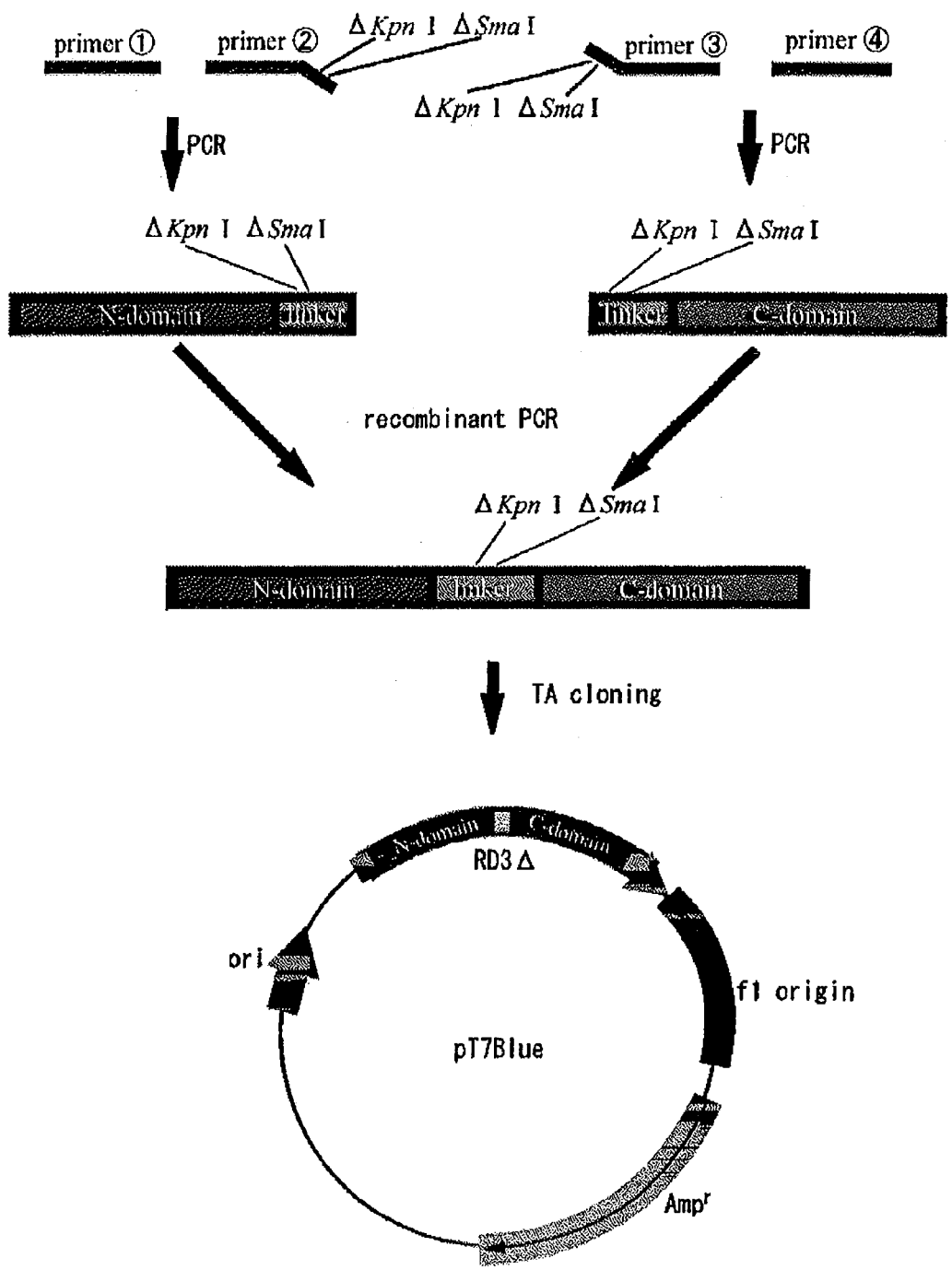
FIG. 3 schematically shows the process for constructing the DNA sequence of RD3Δ in which restriction site i.e., KpnI and SmaI sites, in the linker portion of RD3 have been deleted.

Hereinafter, the present invention will be described in detail.

In the present invention, the example of antifreeze protein to be multimerized includes, but not limited to, fish-derived AFP (for example, Type I AFP, Type II AFP, Type III AFP and Type IV AFP), plant-derived AFP and insect-derived AFP. For example, three insect AFPs have been characterized in detail. The spruce budworm (*Choristoneura fumiferana*) AFP is left-handed β-helical protein consisting of 15-amino acid loops with a repetitive Thr-X-Thr motif.

The beetle, *Tenebrio molitor*, AFP is right-handed β-helical protein comprised of seven or eight tandem repeats of a 12-amino acid sequence (Thr-Cys-Thr-X-Ser-X-X-Cys-X-X-Ala-X) (SEQ ID NO: 20). The beetle, *Dendroides canadensis*, AFP is homologous to *Tenebrio molitor* AFP.

The amino acid sequence or the number of amino acid residues of the peptide linker used for multimerizing such antifreeze proteins is not particularly limited, and examples thereof include a polypeptide linker constituted of nine amino acid residues (Asp-Gly-Thr-Thr-Ser-Pro-Gly-Leu-Lys) (SEQ ID NO: 19) which is observed in the RD3 protein.

In order to produce the multimerized antifreeze protein of the present invention, DNA encoding a multimerized antifreeze protein is prepared, then incorporated the DNA into a suitable vector, then transformed, for example, bacteria with the vector, and then the transformant is cultured, thereby obtaining the multimerized antifreeze protein. Alternatively, this multimerized antifreeze protein may be synthesized using conventional peptide synthesizers, instead of using gene recombination techniques as mentioned above.

A means for obtaining the multimerized antifreeze protein of the present invention is described in more detail with reference to examples using gene recombination techniques.

For example, in order to obtain a multimerized antifreeze protein having a structure such as Type III AFP-linker-Type III AFP-linker-Type III AFP (hereinafter referred to as "RD3 NCC") or Type III AFP-linker-Type III AFP-linker-Type III AFP-linker-Type III AFP (hereinafter referred to as "RD3 NCNC"), a DNA sequence encoding the fish-derived Type III AFP in which codon is optimized for a bacterial host or the like is used to construct a DNA sequence encoding AFPs which is tetramerized and trimerized vis peptide linkers comprising nine amino acid residues. Subsequently, the bacterial host or the like is transformed with a vector prepared by cloning this DNA sequence. The transformant is then induced to express by isopropyl-β-D(−)-thiogalactopyranoside and the like, and the expressed recombinant is purified by ion-exchange chromatography. Thus, RD3 NCC or RD3 NCNC can be obtained.

The amino acid sequence of RD3 NCNC is shown as SEQ ID NO: 2. The amino acid sequence of RD3 NCC is shown as SEQ ID NO: 4. The multimerized antifreeze protein of the present invention include a protein in which mutation is introduced in the amino acid sequence shown as SEQ ID NO: 2 or 4 without decreasing or losing an antifreeze activity of the original protein (i.e. a protein comprising an amino acid sequence as shown in SEQ ID NO: 2 or 4 having deletion, substitution, or addition of one or more amino acids and having an antifreeze activity). Examples of such mutation include, but are not limited to, naturally-occurring and artificial mutations. An example of a technique to cause an artificial mutation is, but is not limited to, site-specific mutagenesis (see, Nucleic Acids Res. 10, 6487–6500, 1982). The number of amino acids mutated is not limited, provided that it does not lose an antifreeze activity of the protein. "One or more amino acids" means within 30 amino acids, preferably within 20 amino acids, more preferably within 10 amino acids, and most preferably within 5 amino acids.

The nucleotide sequence encoding RD3 NCNC is shown as SEQ ID NO: 1. The nucleotide sequence encoding RD3 NCC is shown as SEQ ID NO:3. The DNA which hybridizes to a DNA complementary to a DNA consisting of all or a portion of a nucleotide sequence as shown in SEQ ID NO: 1 or 3 under stringent conditions, and having an antifreeze activity is also emcompassed in the present invention. "Stringent conditions" means conditions under which only specific hybridization occurs and non-specific hybridization does not occur. Such conditions are generally "1×SSC, 0.1% SDS, 37° C.", preferably "0.5×SSC, 0.1% SDS, 42° C.", more preferably "0.2×SSC, 0.1% SDS, 65° C.". A DNA obtained by such hybridization generally shows high homology with a DNA comprising a nucleotide sequence as shown in SEQ ID NO: 1 or 3. The term "high homology" used herein means 60% or more of homology, preferably 75% or more of homology, and more preferably 90% or more of homology.

The antifreeze activities of the RD3 NCNC and RD3 NCC can be determined by observing the ice growth inhibitory activity under a microscope or measuring the antifreeze activity using a cryoscopic osmometer.

Figure 14:
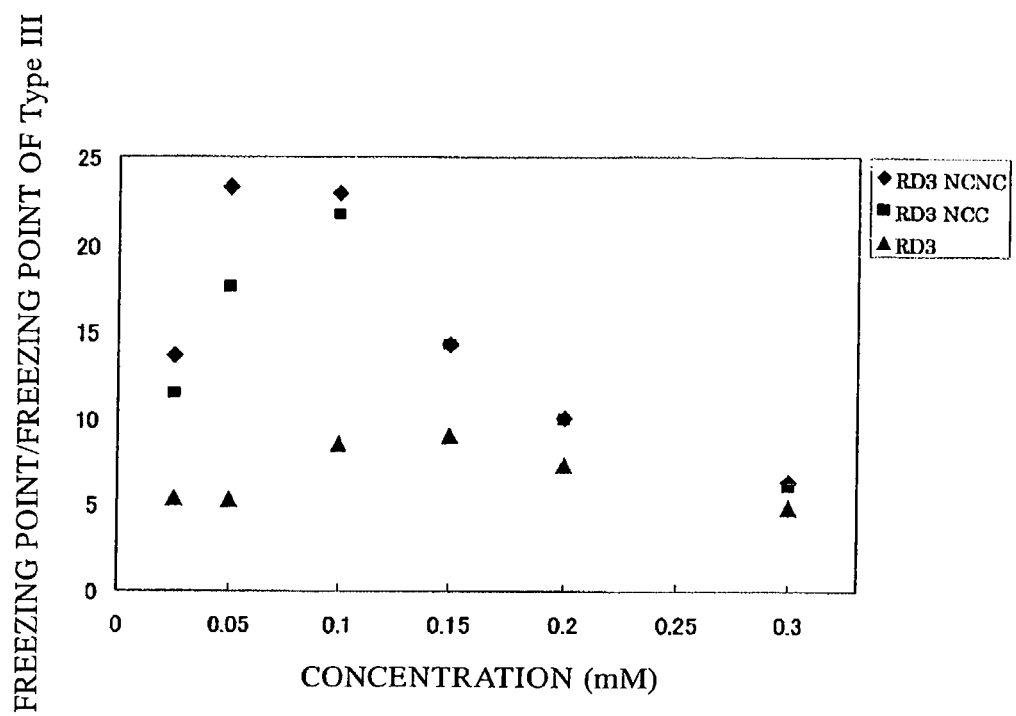
FIG. 14 shows the levels of antifreeze activity of RD3 NCNC, RD3 NCC, and RD3 with respect to Type III AFP.

The thus obtained RD3 NCNC and RD3 NCC proteins of the present invention caused the thermal hysteresis effect per molecule to increase by at least approximately 20 times particularly in the low concentrations (approximately 0.05 to 0.1 mM), and exhibited very high antifreeze activities compared to RD3 (FIG. 14). Further, the RD3 NCNC and RD3 NCC proteins efficiently inhibited ice nuclei growth in low concentrations (FIGS. 12C, D).

As is apparent from the foregoing description, multimerization of antifreeze proteins can significantly improve thermal hysteresis activity and ice recrystallization inhibitory activity. Even a small amount of multimerized antifreeze protein of the present invention sufficiently exhibits antifreeze activities. Accordingly, the present invention relates to very practical and effective techniques for accelerating the use of antifreeze proteins in, for example, quality maintenance of frozen foods such as ice creams, cryopreservation of cells and tissues, or prevention of pipe freeze of the cooling systems, cold storages, or the like.

This specification includes part or all of the contents as disclosed in the specification and/or drawings of Japanese Patent Application No.2001-400607, which is a priority document of the present application.

PREFERRED EMBODIMENTS OF THE INVENTION

Examples of the present invention are given below, although the present invention is not particularly limited by these examples.

EXAMPLE 1

Design of RD3 NCNC and RD3 NCC

AFP (RD3 NCNC), which was prepared by ligating two RD3s via a polypeptide linker constituted of nine amino acid residues (Asp-Gly-Thr-Thr-Ser-Pro-Gly-Leu-Lys) (SEQ ID NO: 19), and AFP (RD3 NCC), which was prepared by ligating the C-domain to RD3 via a linker, were designed. Three amino acid residues at the N-terminus of the domain ligated to downstream of the linker were deleted (FIGS. 1, 2). The molecular weight of RD3 NCNC is calculated to be 29.6 KDa and the molecular weight of RD3 NCC is calculated to be 22.2 KDa.

EXAMPLE 2

Construction of Synthetic Gene Encoding RD3 NCNC or RD3 NCC

A DNA sequence encoding RD3 NCNC or RD3 NCC antifreeze proteins, which were optimized for expression in *E. coli*, was constructed as follows. A DNA fragment on the sense-strand side, which was optimized for a codon usage of E. coli, and a DNA fragment on the antisense-strand side, which was similarly optimized for a codon usage of E. coli, were annealed and ligated to each other to construct a DNA sequence encoding the RD3 which was preared by ligating an N-domain-linker and a linker-C-domain (Kazunori Miura et al., 1999. J. Biochem. 126: 387–394, SEQ ID NO: 5). The DNA sequence encoding the RD3 was then cloned into a vector. The DNA sequence encoding the N-domain and the C-domain in which restriction sites, i.e., KpnI and SmaI sites, in a linker of RD3 were deleted by silent mutation, was amplified by PCR using the cloned vector as a template and the primers as shown below.

```
                                            (SEQ ID NO: 7)
primer 1  5'-GAGCTGCAGTTAACTTTAAG-3'
              Pst I (SEQ ID NO: 8)
primer 2  5'-ACCCGGAGAGGTGGTGCCGTCTTCGTAGTTTTTA-3'
              ΔSma I      ΔKpn I (SEQ ID NO: 9)
primer 3  5'-AGACGGCACCACCTCTCCGGGTCTGAAATCCGTTG-3'
              ΔKpn I       ΔSma I (SEQ ID NO: 10)
primer 4  5'-TTCGAGCTCCACCGCGGTGGCG-3'
              Sac I BstX I Sac II
```

Subsequently, these PCR products were purified by agarose gel electrophoresis to perform recombinant PCR. Approximately 420 bp structural gene of RD3 was purified from the electrophoresed agarose gel and cloned into a pT7Blue vector (Novagen) using adenine added to the 3' terminus (TA cloning). Thus, the structural gene of RD3 (RD3Δ) having deleted restriction sites, i.e., KpnI and SmaI sites, in the linker portion was constructed (FIG. 3). E. coli DH5α strain was transformed with this vector, and after proliferation, plasmid DNA was isolated by the alkali-SDS method. A DNA sequence encoding RD3 having a portion of the linker containing the SmaI site added to its C terminus (RD3 NC1), was amplified using the plasmid DNA as a template and the primers as shown below (FIG. 4).

```
primer 1
5'-GAGCTGCAGTTAACTTTAAG-3'         (SEQ ID NO: 11)
       Pst I primer 5
5'-GTCCCCCGGGGAGGTGGTGCCGTCTTCGTAG  (SEQ ID NO: 12)
TTTTTAACCATGTCCGGCATCAGGGTCTG-3'
          Sma I      ΔKpn I
```

Figure 4:
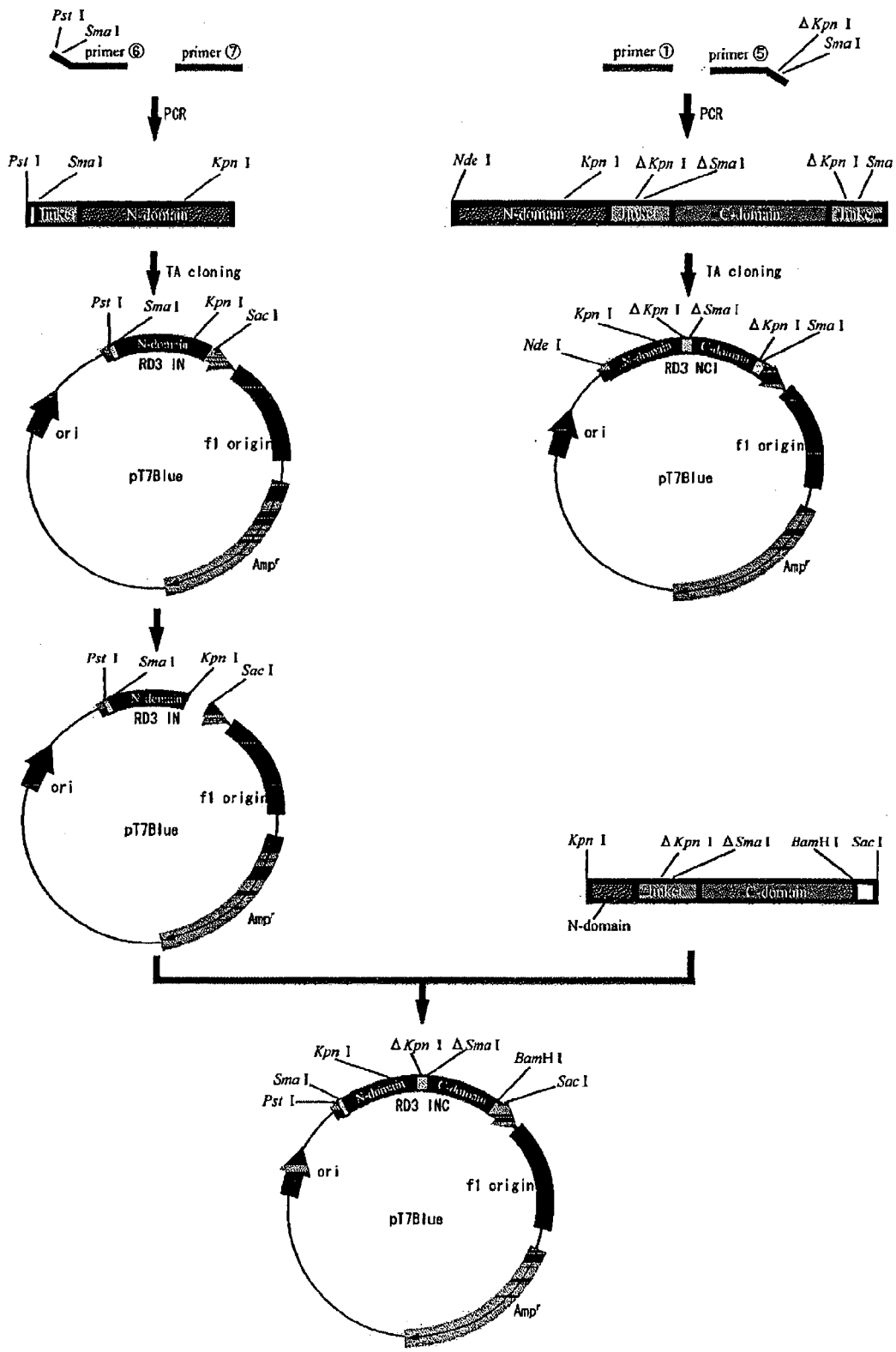
FIG. 4 schematically shows the process for constructing the DNA sequence having a portion of a linker ligated to the N-terminal side of RD3 and the DNA sequence having a portion of a linker ligated to the C-terminal side of RD3.

A DNA sequence of the N-domain having a portion of a linker added to its N terminus (RD3 1N) was amplified using the DNA sequence of the RD3 N-domain as a template and the primers as shown below (FIG. 4).

```
primer 6
                                            (SEQ ID NO: 13)
5'-GGAACTGCAGCCCGGGTCTGAAATCCGTTGTTGCTAACCAG-3'
       Pst I  Sma I primer 7
                                            (SEQ ID NO: 14)
5'-CGCGGATCCTATTCGTAGTTTTTAACCATG-3'
       BamH I
```

Figure 5:
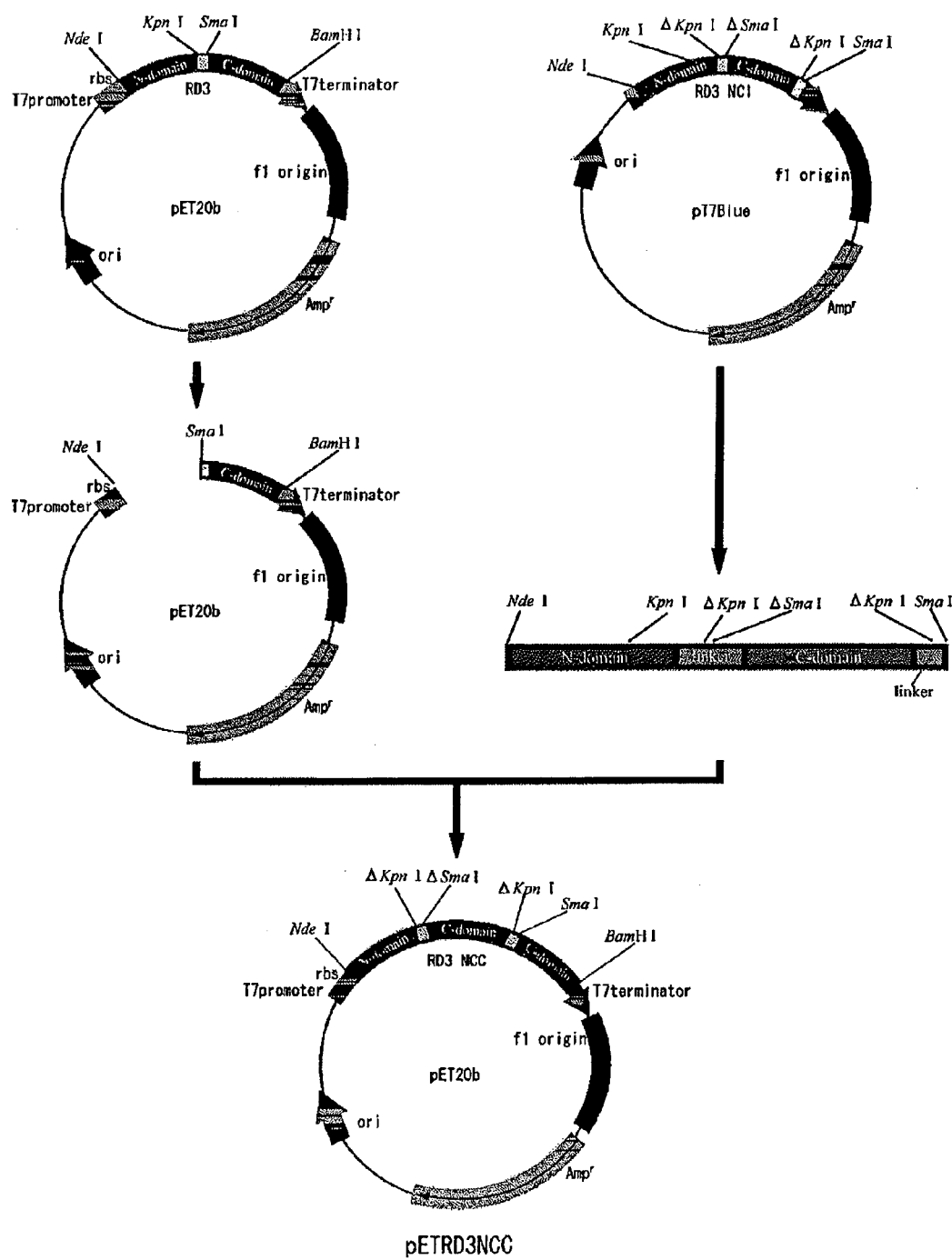
FIG. 5 schematically shows the process for constructing the RD3 NCC expression vector, pETRD3NCC.
Figure 6:
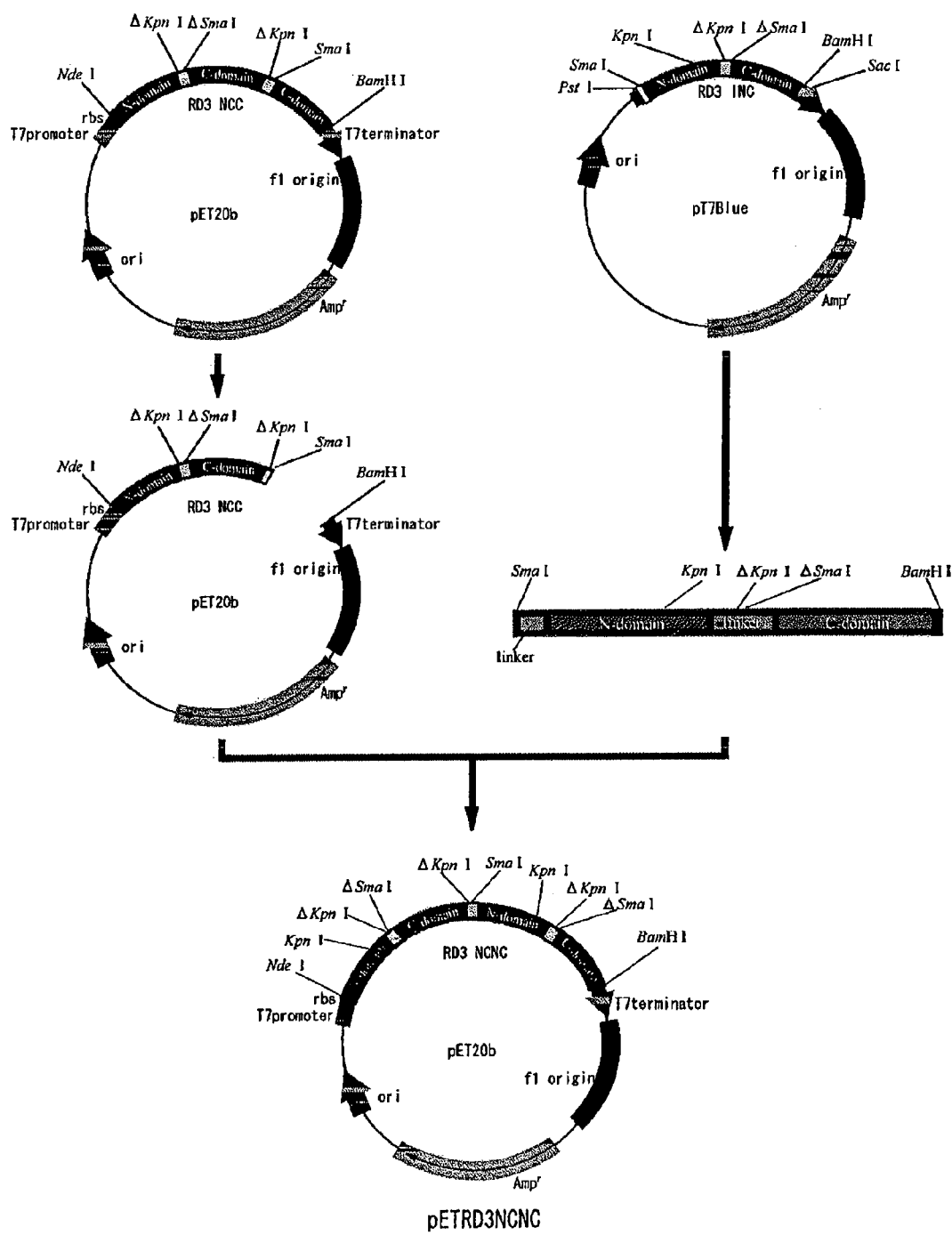
FIG. 6 schematically shows the process for constructing the RD3 NCNC expression vector, pETRD3NCNC.

Each of the PCR products was purified and then introduced into a vector by TA cloning. RD3 1N inserted into plasmid DNA was amplified with E. coli, and the structural gene of RD3 having a portion of the linker added to its N terminus (RD3 1NC) was constructed using already existing restriction sites, i.e., KpnI and SacI sites (FIG. 4). DNA fragments encoding RD3 NC1 are then ligated to conventional RD3 expression vector, pET20bRD3, to construct RD3 NCC expression plasmid DNA, pETRD3NCC (FIG. 5). Subsequently, DNA fragments of RD3 1NC were introduced into this vector to construct the RD3 NCNC expression plasmid DNA, pETRD3NCNC (FIG. 6).

EXAMPLE 3

Determination of Gene Sequences of Constructed RD3 NCNC and RD3 NCC

The DNA sequences of RD3 NCNC and RD3 NCC were determined in accordance with the protocol provided by ABI PRISM™. In order to determine the sequence of the sense strand of RD3 NCNC, 4 µl of Terminator Ready Reaction Mix (ABI PRISM™), 400 ng of pETRD3NCNC, 2 µl of 5× reaction solution (ABI PRISM™), and 3.2 pmol of T7 promoter primer were mixed, and the volume of the mixture was brought to 20 µl with sterilized water. Thereafter, the reaction was carried out using a Thermal Cycler (TAKARA) in accordance with the following program.

| Cycle | Temperature | Time |
|---|---|---|
| 30 | 96.0° C. | 10 sec. |
|  | 50.0° C. | 5 sec. |
|  | 60.0° C. | 4 min. |
| 1 | 4.0° C. | (until the samples were collected) |

In order to determine the sequence of the antisense strand of the RD3 NCNC gene, 4 µl of Terminator Ready Reaction Mix (ABI PRISM™), 400 ng of pETRD3NCNC, 2 µl of 5× reaction solution (ABI PRISM™), and 3.2 pmol of T7 terminator primer were mixed, and the volume of the mixture was brought to 20 µl with sterilized water. Thereafter, the reaction was similarly carried out. After the completion of the reaction, 2 µl of 3M sodium acetate (pH 5.2) and 50 µl of 95% ethanol were added to the sample, and the mixture was allowed to stand at room temperature for 15 minutes. The mixture was then centrifuged at 12,000 rpm for 20 minutes, and reaction products were collected as precipitates. 250 µl of 70% ethanol was added to this precipitate, the mixture was centrifuged at room temperature at 12,000 rpm for 5 minutes, and the resulting precipitates were collected thereby washing the reaction products. Further, the reaction products were solidified by a centrifugal evaporator, dissolved in 15 µl of Template Suppression Reagent (ABI PRISM™), heated at 95° C. for 2 minutes, and then quenched in ice. This sample was set in the ABI PRISM 310 (ABI PRISM™), and the DNA sequence of RD3 NCNC was determined. As a result, the sequence as shown in FIG. 7 was determined, and the construction of the sequence of interest was confirmed.

The gene sequence of RD3 NCC was similarly determined (FIG. 8).

EXAMPLE 4

Expression of RD3 NCNC and RD3 NCC with *E. coli*

*E. coli* BL21 (DE3) was transformed with plasmid pETRD3NCNC. Since plasmid pETRD3NCNC comprises an ampicillin resistant gene introduced therein, *E. coli* was plated in an ampicillin-containing LB agar medium and incubated at 37° C. overnight, thereby selecting a transformant. One of the formed colonies was inoculated in 2 ml of the LB medium containing 100 μg/ml ampicillin and cultured at 20° C. overnight. This culture medium was subcultured in 100 ml of the LB medium containing 100 μg/ml ampicillin and further cultured at 20° C. overnight. 20 ml out of 100 ml of culture medium was subcultured in 2,000 ml of the LB medium containing 100 μg/ml ampicillin and cultured at 20° C. while monitoring the growth rate of *E. coli* by observing the absorbance at 600 nm. When the absorbance at 600 nm reached 0.5, isopropyl-β-D(−)-thiogalactopyranoside was added to the culture to a final concentration of 0.5 mM. Thus, the expression of antifreeze proteins was induced, and cultivation was continued for an additional 8 hours. The culture medium was centrifuged at 3,600×g at 4° C. for 15 minutes to collect bacterial cells. The bacterial cells were suspended in 10 mM tris-hydrochloric acid buffer/1 mM disodium ethylenediaminetetraacetate (pH 8.0, TE buffer), followed by ultrasonic disruption in ice. This disrupted product was centrifuged at 11,900×g at 4° C. for 30 minutes to separate into soluble fractions and insoluble fractions. RD3 NCNC was extracted from the insoluble fraction with the aid of 100 mM tris-hydrochloric acid buffer (pH 8.5)/6 M guanidine hydrochloride. RD3 NCC was similarly extracted.

EXAMPLE 5

Purification of RD3 NCNC and RD3 NCC

Figure 9:
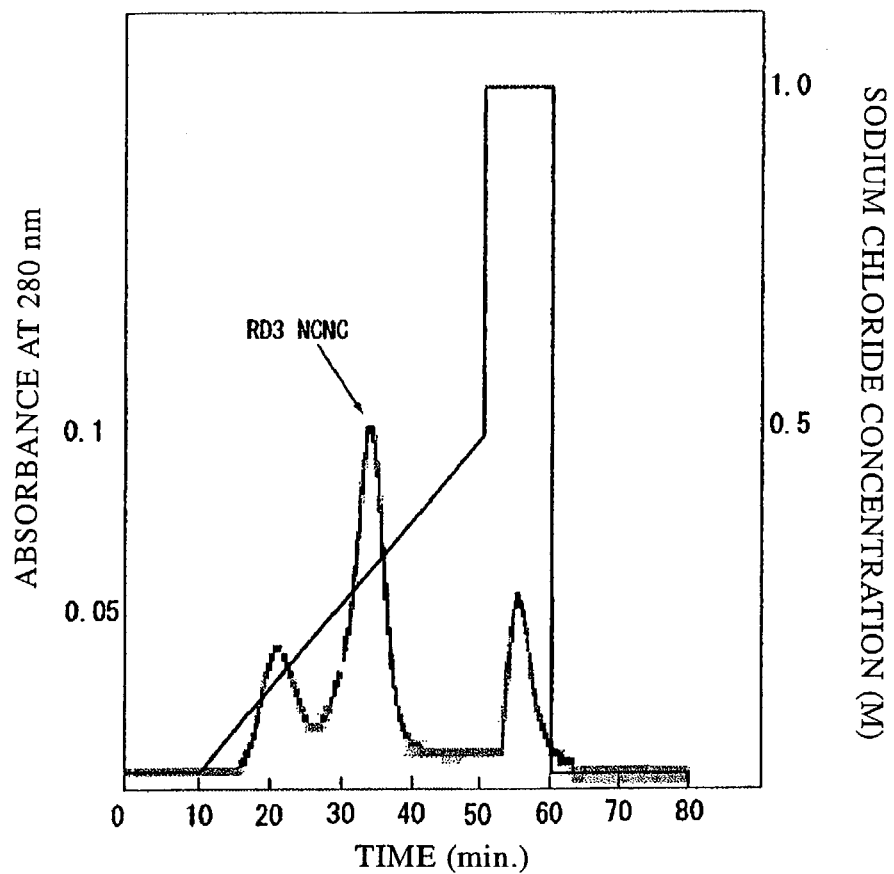
FIG. 9 shows a elution pattern of RD3 NCNC in cation exchange chromatography.
Figure 10:
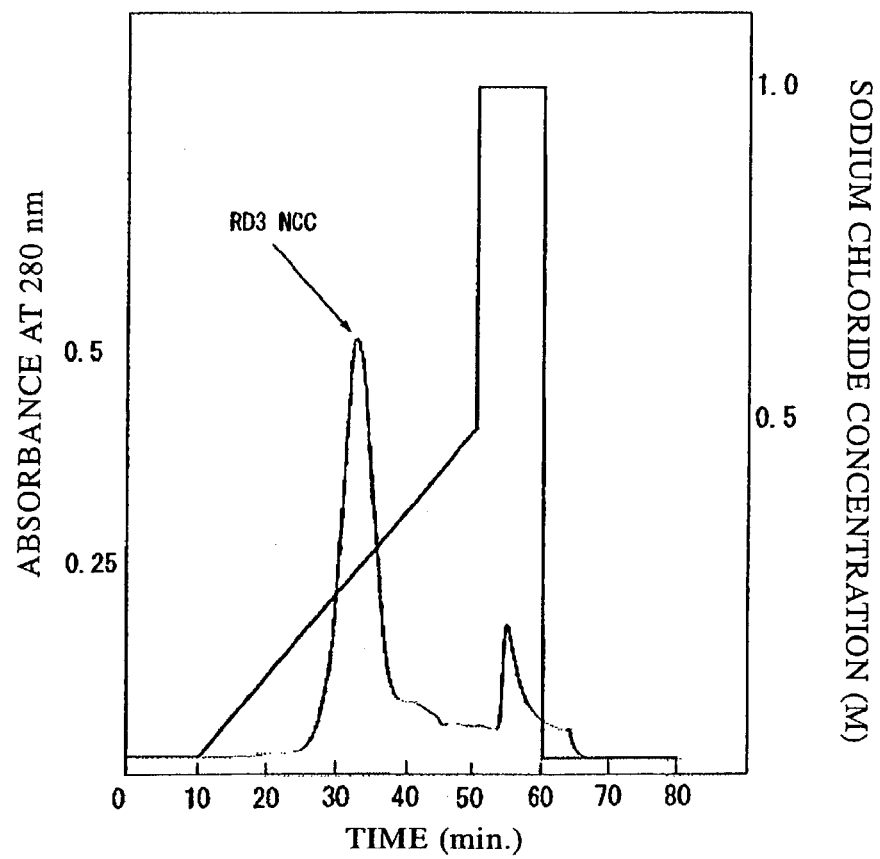
FIG. 10 shows a elution pattern of RD3 NCC in cation exchange chromatography.

RD3 NCNC extracted from the insoluble fraction was diluted 20-fold with the aid of 50 mM dibasic potassium phosphate/100 mM sodium chloride (pH 10.7), and the diluted product was allowed to stand at 4° C. for 4 to 7 days, thereby inducing protein refolding. This refolded RD3 NCNC and the soluble fraction of the buffer were substituted with 50 mM sodium acetate (pH 3.7) by dialysis, causing contaminant proteins to aggregate and precipitate. Precipitates were removed by centrifugation at 11,900×g at 4° C. for 30 minutes. Cation exchange chromatography was performed in a chromatography chamber at 4° C. by connecting the FPLC system (Amersham Pharmacia Biotech) with High-S column (BIO-RAD). The sample buffer was 50 mM sodium acetate (pH 3.7), and the flow rate was 1 ml/min. RD3 NCNC was eluted using a linear gradient of 0 to 0.5M sodium chloride (Wako Pure Chemicals Industries, Ltd.) (FIG. 9). An eluated sample was detected based on the absorbance at 280 nm using UV-1 (Amersham Pharmacia Biotech) and collected using a fraction collector. The collecting amount per fraction was set at 1 ml. RD3 NCC was similarly purified (FIG. 10).

EXAMPLE 6

Sodium Dodecyl Sulfate-Polyacrylamide Gel Electrophoresis

Figure 11:
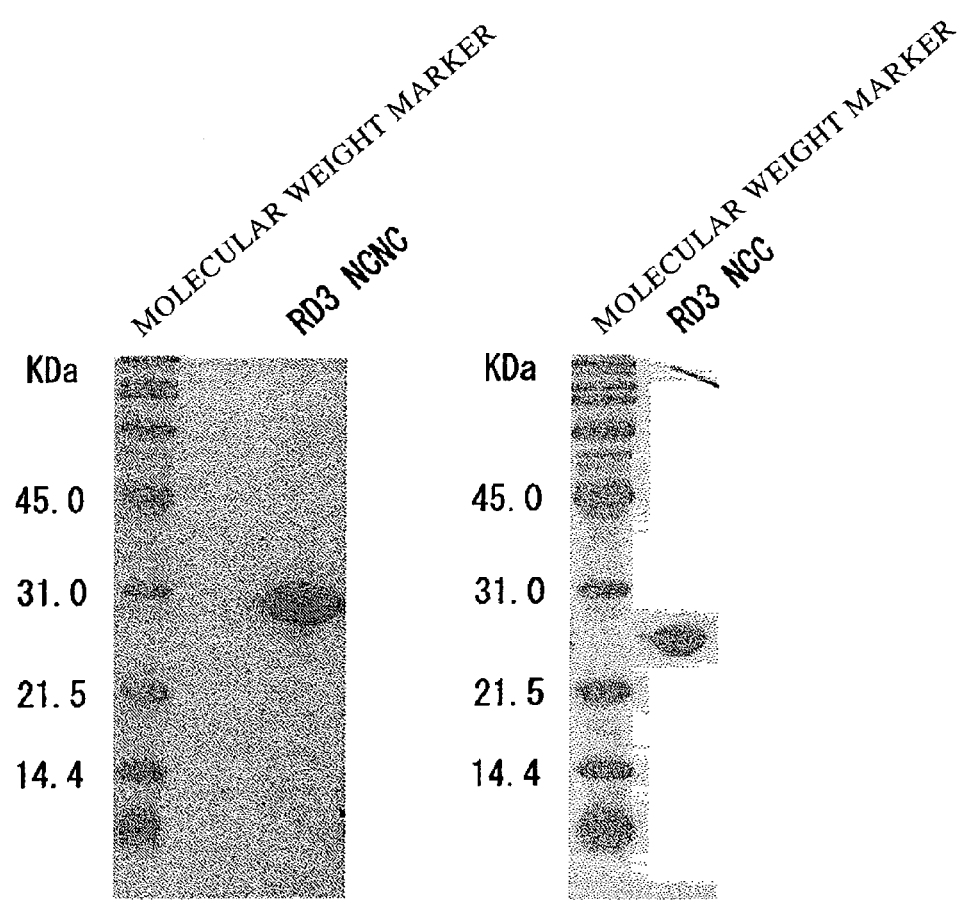
FIG. 11 shows a result of sodium dodecyl sulfate-polyacrylamide electrophoresis of purified RD3 NCNC and RD3 NCC.

In accordance with commonly used protocols, the purified RD3 NCNC and RD3 NCC were electrophoresed in 15% polyacrylamide gel using an electrophoresis apparatus (ATTO). In order to measure the molecular weights, broad range SDS-PAGE standard (BIO-RAD) was simultaneously electrophoresed. 0.065M tris-hydrochloric acid buffer (pH 6.8)/2% sodium dodecyl sulfate/10% sucrose/5% β-mercaptoethanol/0.001% Bromophenol Blue was used as the sample buffer. A stacking gel was prepared by mixing 0.75 ml of 0.5M tris-hydrochloric acid buffer (pH 6.8), 0.45 ml of mixed solution of 30% acrylamide/bis (37.5:1), 0.12 ml of 10% sodium dodecyl sulfate, and 1.78 ml of distilled water, and a separating gel was prepared by mixing 2.25 ml of 1.5M tris-hydrochloric acid buffer (pH 8.8), 4.5 ml of mixed solution of 30% acrylamide/bis (37.5:1), 0.36 ml of 10% sodium dodecyl sulfate, and 1.89 ml of distilled water. A solution of 3.03 g of tris(hydroxymethyl) aminomethane, 14.4 g of glycine, and 1 g of sodium dodecyl sulfate in 1 l of distilled water (in total) was used as the electrophoresis buffer. Gel staining was carried out overnight using a staining solution comprising 20 ml of methanol, 12.5 g of ammonium sulfate, 2.5 ml of phosphoric acid, and 0.04% Coomassie brilliant blue G-250 dissolved in 100 ml of distilled water, and destaining was carried out with distilled water. As shown in FIG. 11, purification of RD3 NCNC with a molecular weight of 29.6 KDa and RD3 NCC with a molecular weight of 22.2 KDa with high purity can be confirmed.

EXAMPLE 7

Observation of Ice Crystal Growth

Figure 12:
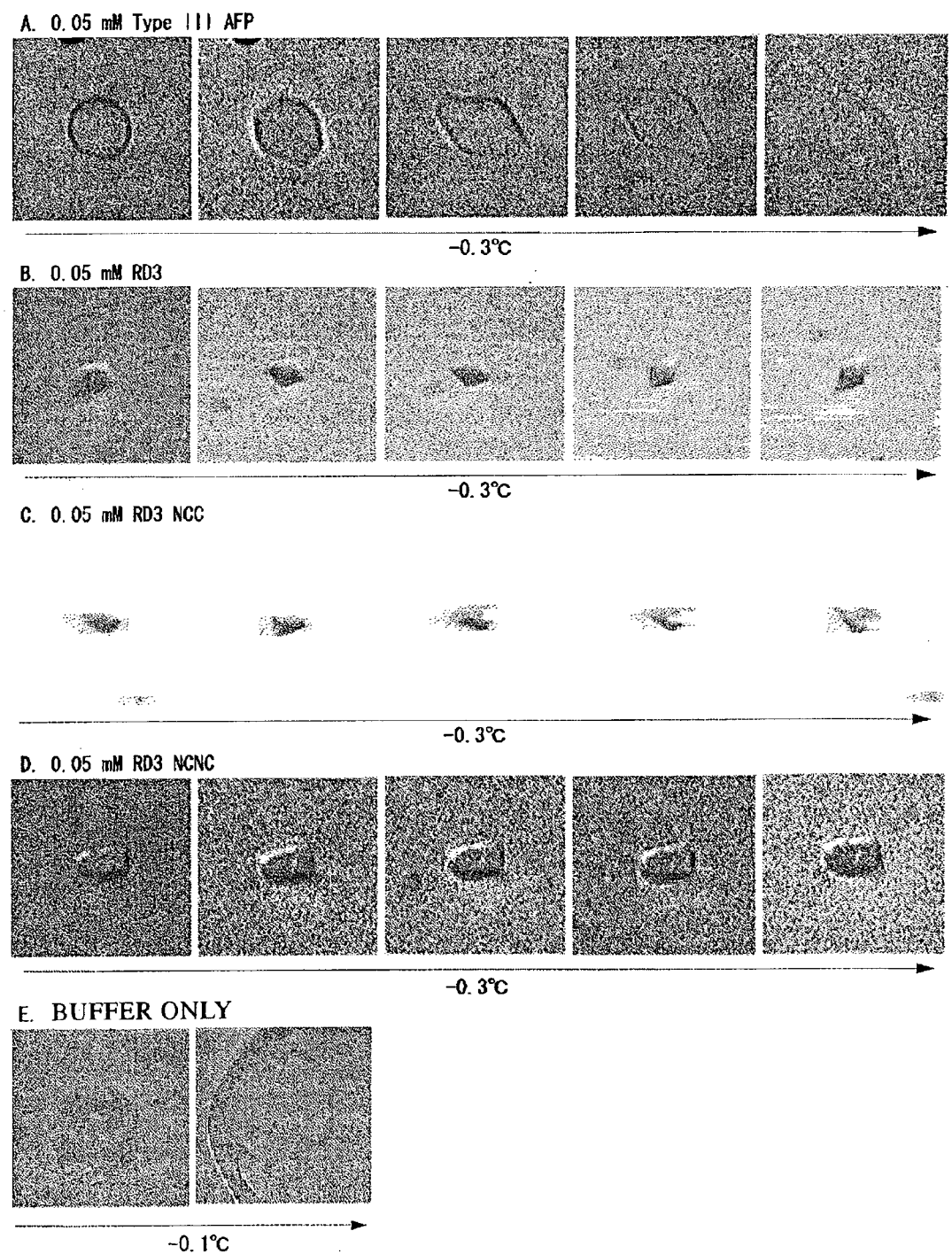
FIG. 12 is a photograph showing the growth process of ice nuclei in a solution containing RD3 NCNC, RD3 NCC, RD3, and Type III AFP.

Samples for observing ice crystal growth were dissolved in a 0.1M ammonium bicarbonate (pH 7.9) buffer at concentrations of 0.05 mM and 0.2 mM. 2 μl of sample solution was placed on a cover glass (diameter 1.6 mm) with a washer (diameter 1.2 mm, thickness 0.8 mm) adhered thereon with nail polish, and a cover glass (diameter 1.25 mm) was further adhered, as a cover, onto the washer also with nail polish. This measuring cell was placed on a Linkam THMS 600 cooling stage, which was installed on the LEICA DMLB microscope, and a cover slip was overlaid. The cooling stage was connected to the Linkam L-600A cooling system, and the temperature on the stage was regulated by the Linkam LK-600PM controller. The sample was cooled to −25° C. (−13° C./min) and frozen, and the sample was then heated until ice melted and only one ice nucleus was left. The sample was gradually cooled (−0.05° C./min), and ice crystal growth was recorded with a high-sensitivity CCD camera system and a video recorder (FIG. 12). It was demonstrated that the multimerized antifreeze protein strongly inhibited ice nuclei growth even in low concentrations.

EXAMPLE 8

Measurement of Freezing Point

Figure 13:
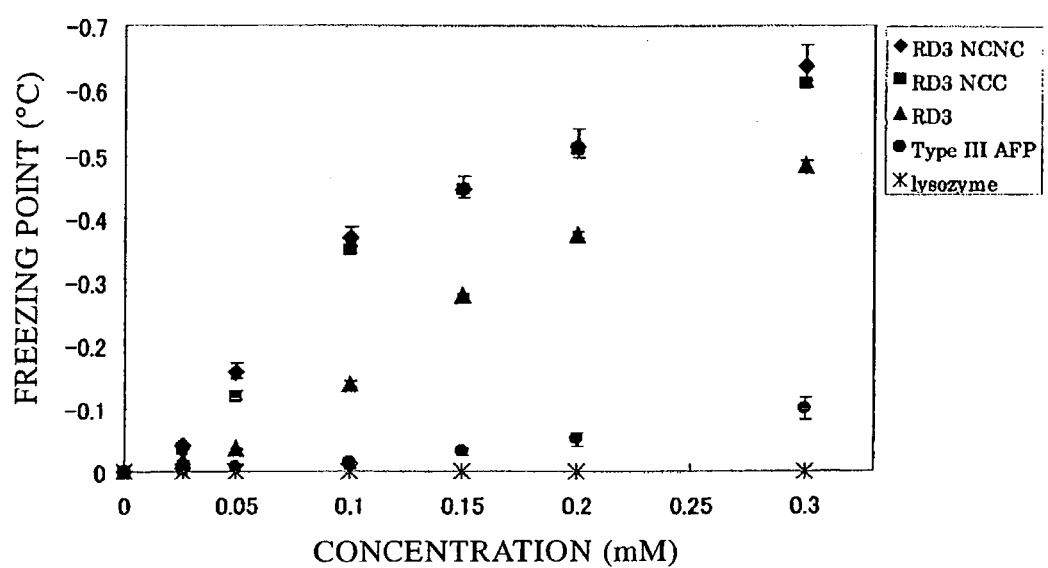
FIG. 13 shows the levels of antifreeze activity of RD3 NCNC, RD3 NCC, RD3, and Type III AFP.

50 μl of samples dissolved in a 0.1M ammonium bicarbonate (pH 7.9) buffer at concentrations of 0.025, 0.05, 0.1, 0.15, 0.2, and 0.3 mM were used, and the total osmotic pressure was measured using a cryoscopic osmometer (VOGEL) to calculate the freezing point (FIG. 13). Levels of activity with respect to Type III AFP are shown in FIG. 14. The prepared RD3 NCNC and RD3 NCC exhibited thermal hysteresis of approximately 20 times as much as that of Type III AFP in low concentrations.

All publications, patents and patent applications cited herein are incorporated by reference in their entirety.

What is claimed is:

1. A multimerized antifreeze protein (AFP) comprising three or more antifreeze proteins or peptides that are ligated by linker peptides and wherein at least one of the antifreeze proteins or peptides is a Type III AEP.

2. A protein comprising an amino acid sequence as shown in SEQ ID NO: 2.

3. A protein comprising an amino acid sequence as shown in SEQ ID NO: 4.

4. A method for producing a multimerized antifreeze protein or peptide, comprising synthesizing the multimerized antifreeze protein according to claim 1 using a peptide synthesizer.

5. A method for producing a multimerized antifreeze protein, comprising synthesizing the multimerized antifreeze protein according to claim 2 using a peptide synthesizer.

6. A method for producing a multimerized antifreeze protein, comprising synthesizing the multimerized antifreeze protein according to claim 3, using a peptide synthesizer.

7. The method of claim 4, wherein the multimerized antifreeze protein comprises Type III AFP.

* * * * *